United States Patent
Campbell et al.

(10) Patent No.: US 12,180,444 B2
(45) Date of Patent: Dec. 31, 2024

(54) CONTAINERS AND METHODS FOR CELL TRANSDUCTION

(71) Applicant: Saint-Gobain Performance Plastics Corporation, Solon, OH (US)

(72) Inventors: Katie Campbell, Northborough, MA (US); Natalie Fekete, Marlborough, MA (US); Rachel Z. Pytel, Newton, MA (US)

(73) Assignee: Saint-Gobain Performance Plastics Corporation, Solon, OH (US)

(*) Notice: Subject to any disclaimer, the term of this patent is extended or adjusted under 35 U.S.C. 154(b) by 413 days.

(21) Appl. No.: 17/136,400

(22) Filed: Dec. 29, 2020

(65) Prior Publication Data
US 2021/0198606 A1    Jul. 1, 2021

Related U.S. Application Data

(60) Provisional application No. 62/954,735, filed on Dec. 30, 2019.

(51) Int. Cl.
| C12M 1/00 | (2006.01) |
| C12M 1/12 | (2006.01) |
| C12N 15/86 | (2006.01) |
| C12N 15/87 | (2006.01) |

(52) U.S. Cl.
CPC ............ *C12M 23/14* (2013.01); *C12M 25/00* (2013.01); *C12N 15/86* (2013.01); *C12N 15/87* (2013.01)

(58) Field of Classification Search
None
See application file for complete search history.

(56) References Cited

U.S. PATENT DOCUMENTS

| 5,686,278 | A | 11/1997 | Williams |
| 6,670,177 | B2 | 12/2003 | Williams |
| 7,790,849 | B2 | 9/2010 | Asada |
| 2004/0265284 | A1 | 12/2004 | Williams |
| 2006/0030046 | A1 | 2/2006 | Asada |
| 2014/0255360 | A1 | 9/2014 | Spencer |
| 2015/0344844 | A1 | 12/2015 | Better |
| 2016/0178490 | A1 | 6/2016 | Civel |
| 2020/0209233 | A1* | 7/2020 | Campbell ............ C12M 23/20 |

FOREIGN PATENT DOCUMENTS

| WO | 2006119054 A2 | 11/2006 |
| WO | 2016112079 A1 | 7/2016 |

OTHER PUBLICATIONS

Y.W. Tong & M.S. Shoichet, "Enhancing the neuronal interaction on fluoropolymer surfaces with mixed peptides or spacer group linkers," Biomaterials, 22, 1029-34 (2001).
H. Hanenberg et al., "Colocalization of retrovirus and target cells on specific fibronectin fragments increases genetic transduction of mammalian cells," Nature Medicine, 2(8), 876-882 (1996).
International Search Report and Written Opinion in PCT/US2020/067282, dated Apr. 27, 2021.
V.P. Patel & H.F. Lodish, "The Fibronectin Receptor on Mammalian Erythroid Precursor Cells: Characterization and Developmental Regulation," J. Cell. Biology, 102, 449-456 (1986).

* cited by examiner

*Primary Examiner* — Nancy J Leith
(74) *Attorney, Agent, or Firm* — McDonnell Boehnen Hulbert & Berghoff LLP (57) ABSTRACT

This disclosure relates generally to containers (such as bags) having surfaces comprising one or more aptamer sequences. More particularly, the present disclosure relates to containers such as bags comprising a fluoropolymer attached to aptamer sequences having binding affinity for one or more biological agents, and to transductions methods using such containers. In one aspect, the disclosure provides a container (e.g., a bag) having an outer surface and an inner surface, the inner surface comprising a fluoropolymer; attached to the fluoropolymer, a plurality of functional groups; and attached to each of at least a portion of the functional groups, a first aptamer sequence having a binding affinity for a viral vector.

16 Claims, 2 Drawing Sheets

CONTAINERS AND METHODS FOR CELL TRANSDUCTION

CROSS-REFERENCE TO RELATED APPLICATIONS

This application claims the benefit of priority of U.S. Provisional Patent Application No. 62/954,735, filed Dec. 30, 2019, which is hereby incorporated herein by reference in its entirety.

BACKGROUND OF THE DISCLOSURE

Field of the Disclosure

This disclosure relates generally to containers (such as bags) having surfaces comprising one or more aptamer sequences. More particularly, the present disclosure relates to containers such as bags comprising a fluoropolymer attached to aptamer sequences having binding affinity for one or more biological agents, and to transductions methods using such containers.

Technical Background

Transduction, the process by which foreign DNA is introduced into a target cell, e.g., by a viral vector, is important in a number of applications. For example, CAR T-cell therapy is a cancer treatment in which a gene encoding a chimeric antigen receptor (CAR) is introduced to T cells collected from a patient by transduction. The modified cells, after expansion and re-introduction to the patient, can bind to and kill cancer cells. Additionally, viral transduction is regularly used in basic genetic research.

However, gene transfer from a viral vector can be inefficient for certain cell types, such as hematopoietic cells and other suspension cells. Conventionally, transduction efficiency for such systems can be improved by use of an enhancer such as polybrene, protamine sulfate, or retronectin. Polybrene and protamine sulfate improve transduction efficiency by modifying the surface properties of target cells. However, these types of enhancers can negatively impact cell viability. Alternatively, retronectin—a polypeptide that includes a heparin-binding domain having a binding affinity for viral particles and two cell-binding domains having a binding affinity for VLA-4 and VLA-5 surface receptors—can improve transduction efficiency by facilitating co-localization of viral vectors and target cells.

Conventionally, transduction enhancers such as retronectin must be manually coated onto a container before a transduction process. Because the coated containers require special refrigeration and have a short shelf life, the relatively costly, time-consuming coating process typically must be performed by the user conducting the transduction process, shortly before the process.

Accordingly, there remains a need for simple, cost-effective, and/or time-effective system for cell transduction.

SUMMARY OF THE DISCLOSURE

In one aspect, the disclosure provides a container (e.g., in the form of a bag) having an outer surface and an inner surface, the inner surface comprising
a fluoropolymer;
attached to the fluoropolymer, a plurality of functional groups; and
attached to each of at least a portion of the functional groups, a first aptamer sequence having a binding affinity for a viral vector.

In another aspect, the disclosure provides a transduction method, comprising including a viral vector and a target cell in a container as described herein.

Other aspects of the disclosure will be apparent to the person of ordinary skill in the art in view of the disclosure herein.

DETAILED DESCRIPTION

In various aspects, the disclosure relates to containers having an inner surface comprising a fluoropolymer having a plurality of functional groups attached thereto, and a first aptamer sequence attached to each of at least a portion of the functional groups. The containers of the disclosure can be provided in a number of forms. One especially convenient form is a bag, e.g., formed from one or more sheets of fluoropolymeric material as described herein. The person of ordinary skill in the art will be familiar with bag structures such as those used in cell culture, and will be able to adapt conventional bag structures for use in bags and methods of the disclosure based on the description herein Of course, the person of ordinary skill in the art will appreciate that the containers of the disclosure can be provided in a number of other forms, e.g., flasks, tubes, dishes.

Figure 1:
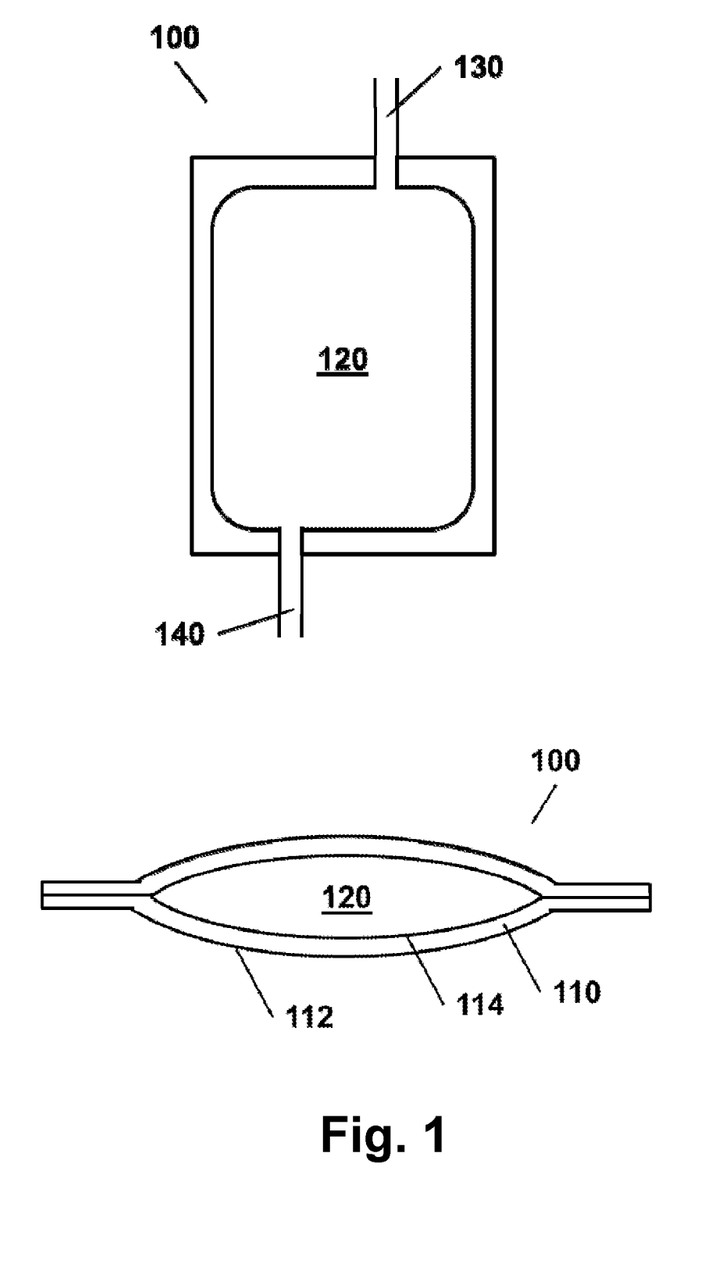
FIG. 1 is a schematic top-down (top) and cross-sectional (bottom) view of a bag according to one embodiment of the disclosure.

One embodiment of such a container, in the form of a bag, is shown in schematic top-down view (top) and cross-sectional view (bottom) in FIG. 1. Bag 100 of FIG. 1 includes a bag wall 110 having an outer surface 112 and an inner surface 114, and further includes ports 130 and 140, located at opposite ends of the bag for adding or removing media to or from the bag. The person of ordinary skill in the art will appreciate that the number and location of ports are not particularly limited, and accordingly can be positioned, for example, for convenience of use or manufacture. Bag 100 can be the product of bonding two fluoropolymer-containing sheets (e.g., two sheets having a layer of fluorinated ethylene propylene on an inside surface thereof) together at their edges (e.g., by laser welding, corona discharge, radiation, heat or melt lamination, etching, plasma treatment, wetting, adhesives, or combinations thereof) to form compartment 120. Ports 130 and 140 can be sealable to provide a sealed compartment 120.

Bag wall 110 can be uniform in its composition, or alternatively can include two or more distinct domains (e.g., two or more layers). For example, bonding two fluoropolymer sheets together, then coating the bonded sheets can provide an outer surface 112 differing in composition from inner surface 114. Similarly, bonding two multi-layer sheets together can provide an outer surface 112 differing in composition from inner surface 114. Multilayer sheets can be formed of both fluoropolymeric and nonfluorinated polymer materials; in such cases, a fluoropolymer layer can be provided at the inner surfaces of one or more of the multi-layer sheets. The thickness of bag wall 110, the volume of compartment 120, and the shape of bag 100 and/or compartment 120 are not particularly limited, and can be selected for convenience of use or manufacture, and/or to suit a specific application. For example, the thickness of the container wall can in certain embodiments be within the range of 0.0003 inches to 0.2 inches, and the volume of the compartment can in certain embodiments be within the range of 100 mL to 100 L.

Figure 2:
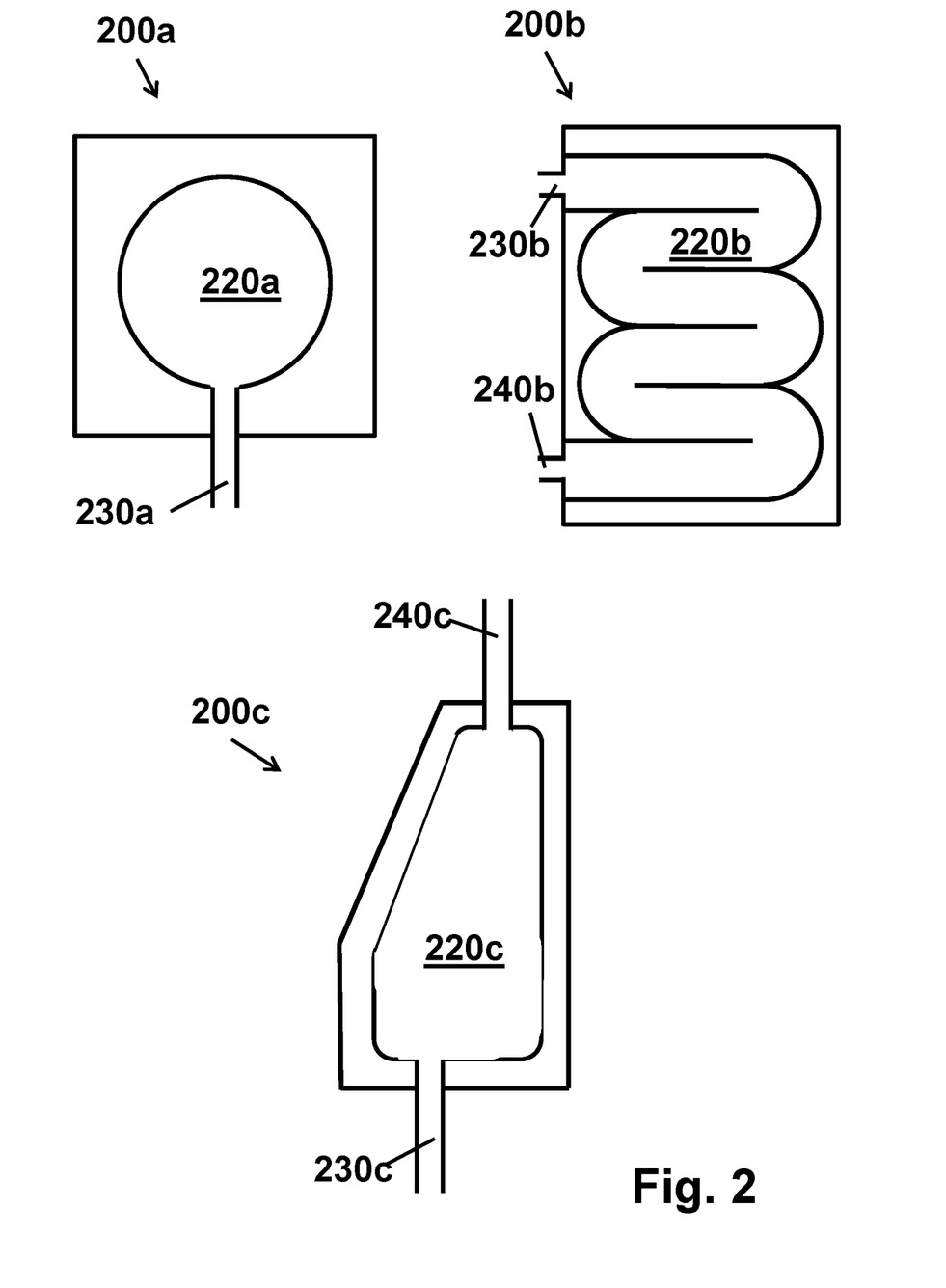
FIG. 2 is a schematic top-down view of bags according to certain embodiments of the disclosure.

FIG. 2 shows several exemplary embodiments of configurations for culture bags suitable for use in the bags and methods of the disclosure. Bag 200a has only a single port 230a, providing access to compartment 220a. Bag 200b is in the so-called "serpentine" configuration, in which a longer path length through the system can be provided; ports 230b and 240b are connected by a serpentine path formed by serpentine-shaped compartment 220b formed by appropriate welding of the sheets forming the bag. And bag 200c has a non-rectangular shape, with a corresponding non-rectangular compartment 220c between ports 230c and 240c.

One or more of the walls of the container can be porous, and can, for example, be permeable to gases produced and consumed in a cell culture (e.g., $O_2$, $CO_2$) but impermeable to liquids (e.g., water). This can allow for passive exchange of gases across the container walls with the atmosphere to allow for respiration of cells in the bag.

The containers of the disclosure are desirably formed such that there is substantially no contamination of a fluid within the container. Accordingly, it is desirable for the inner surface of the container to be formed from materials that will not leach organics into the fluid. For example, in certain embodiments as otherwise described herein, an inner surface of the container wall is formed of a polymer (e.g., a fluoropolymer such as fluorinated ethylene propylene) having a total organic carbon (TOC) in water of less than 0.1 $mg/cm^2$ (e.g., less than 0.05 $mg/cm^2$, or less than 0.05 $mg/cm^2$). Such containers are described, e.g., in U.S. Patent Application Publications nos. 2016/0178490 and 2016/0178491, each of which is hereby incorporated herein by reference in its entirety; the person of ordinary skill in the art can, based on the description herein, adapt such containers for use in the containers and methods of the present disclosure.

As used herein, TOC is measured for a container employed in a system of the disclosure including, for example by extraction from an internal surface area of the container (with results reflected as $mg/cm^2$ are for the TOC per square centimeter of the internal area). TOC is measured according to US Pharmacopeia (USP) 643 and with equipment that utilizes a high temperature wet oxidation reaction of UV-promoted chemical oxidation (*Ultra-Clean Technology Handbook: Volume 1: Ultra-Pure Water*, Ohmi, Tadahiro; CRC Press, 1993, pp. 497-517). Purified water is placed in contact with the polymer for 24 hours at 70° C., for example at a ratio of 3 $cm^2$ of article surface area to 1 mL of water. The water is removed from contact with the polymer and tested in a TOC analyzer. A suitable piece of equipment is a TEKMAR DOHRMANN Model Phoenix 8000 TOC analyzer.

As noted above, the inner surface of the container comprises a plurality of functional groups attached to the fluoropolymer. For example, the fluoropolymer of the inner surface may be functionalized with carboxy groups, hydroxyl groups, aldehyde groups, carbonyl groups, amine groups, imine groups, amide groups, ester groups, anhydride groups, thiol groups, disulfides groups, phenol groups, guanidine groups, thioether groups, indole groups, imidazole groups, aminoethyl amide groups, alkyne groups, alkene groups, aziridine groups, epoxy groups, isonitrile groups, isocyanide groups, tetrazine groups, diazonium surface groups, alkyne groups, alkene groups, aziridine groups, epoxy groups, isonitrile groups, isocyanide groups, tetrazine groups, alkyl groups, aminoethyl amide groups, ester groups, or any mixture thereof. For example, in certain such embodiments, the functional groups include aldehyde groups. In certain embodiments as otherwise described herein, the functional groups include nitrogen-containing groups. For example, in certain such embodiments, the inner surface of the container comprises a plurality of amine groups. The person of ordinary skill in the art will understand that these "functional groups" are identified as the group to which the aptamer sequence is attached; e.g., an "amine" functional group can be attached to a carboxy-bearing aptamer sequence to form a carboxamide bond to the aptamer sequence.

The person of ordinary skill in the art will appreciate that functional groups can be provided at a fluoropolymer surface in many ways. In certain embodiments as otherwise described herein, the functional groups at the inner surface of the container are the product of etching of the fluoropolymer. For example, in certain such embodiments, the etching comprises chemical etching, physical-mechanical etching, or plasma etching. For example, in certain embodiments, the functional groups comprising the inner surface are the product of chemical etching of the fluoropolymer. In certain such embodiments, the chemical etching comprises etching with sodium ammonia or sodium naphthalene. In another example, in certain embodiments, the functional groups comprising the inner surface are the product of physical-mechanical etching. In certain such embodiments, the physical-mechanical etching comprises sandblasting or air abrasion with silica. In another example, the functional groups comprising the inner surface are the product of plasma etching. In certain such embodiments, the plasma etching comprises etching with reactive plasmas such as hydrogen, oxygen, acetylene, methane, and mixtures thereof with nitrogen, argon, and helium.

In certain embodiments as otherwise described herein, the functional groups at the inner surface of the container are the product of activation of the fluoropolymer in the presence of a reactive species. For example, in certain such embodiments, the activation is plasma activation. In certain embodiments, plasma activation includes formation of reactive species on the fluoropolymer by treatment with gases such as, for example, argon, hydrogen, nitrogen, carbon dioxide, oxygen and mixtures thereof. In certain embodiments, plasma activation generates radicals and/or peroxides on a fluoropolymer. Plasma activation can, in certain embodiments, be performed at a pressure within the range of 0.1 Torr to 0.6 Torr, or within the range of 700 Torr to 760 Torr. In another example, in certain such embodiments, the activation is corona activation. In certain embodiments, corona activation includes activation of the fluoropolymer under gases such as, for example, argon, nitrogen, hydrogen, and mixtures thereof to form active sites on the fluoropolymer (e.g., susceptible to a reactive species or subsequent chemical treatment). In certain embodiments, the activation (e.g., plasma activation or corona activation) includes a reactive hydrocarbon vapor such as, for example, ketones, alcohols, p-chlorostyrene, acrylonitrile, propylene diamine, anhydrous ammonia, styrene sulfonic acid, carbon tetrachloride, tetraethylene pentamine, cyclohexyl amine, tetra isopropyl titanate, decyl amine, tetrahydrofuran, diethyl triamine, tertiary butyl amine, ethylene diamine, toluene-2,4-diisocyanate, glycidyl methacrylate, triethylene tetramine, hexane, triethyl amine, methyl alcohol, vinyl acetate, methylisopropyl amine, vinyl butyl ether, methyl methacrylate, 2-vinyl pyrrolidone, methylvinylketone, xylene, or mixtures thereof. In certain embodiments as otherwise described herein, activation (e.g., plasma activation) including a polymerizable hydrocarbon vapor selected from, for example, butylene, ethylene, glutaraldehyde, etc., provides a polymer (i.e., comprising a functional group as otherwise described herein) coated onto the fluoropolymer. The person of ordinary skill in the art will appreciate that, in certain embodiments, plasma activation including a polymerizable hydrocarbon vapor (i.e., plasma polymerization) can provide a relatively disorganized, highly cross-linked polymer coating.

In certain embodiments as otherwise described herein, the functional groups at the inner surface of the container are the product of chemically treating an activated fluoropolymer. For example, in certain such embodiments, the activated fluoropolymer is the product of plasma activation or corona activation of the fluoropolymer. In certain such embodiments, the chemical treatment is a chemical reaction such as, for example, grafting polymerization, coupling, click chemistry, condensation, or addition. In certain embodiments, the chemical treatment is grafting polymerization in solution, comprising polymerizing vinyl monomers via radical polymerization (e.g., initiated by radicals generated through plasma activation of the fluoropolymer). In certain such embodiments, the vinyl monomers are selected from, for example, acrylic acid, (meth)acrylates, (meth)alkylacrylates, styrenes, dienes, alpha-olefins, halogenated alkenes, (meth)acrylonitriles, acrylamides, N-vinyl carbazoles, N-vinyl pyrrolidones, and maleic anhydride. For example, radical polymerization of acrylic acid monomers on the fluoropolymer can, in certain embodiments, provide a dense surface of carboxyl groups. In certain embodiments, such polymerized products can be relatively organized (e.g., as compared to plasma-polymerized products).

In certain embodiments as otherwise described herein, the functional groups at the inner surface of the container are the product of coating an activated fluoropolymer. For example, in certain such embodiments, the activated fluoropolymer is the product of plasma activation or corona activation of the fluoropolymer. In certain such embodiments, the coating is wet coating, powder coating, or chemical vapor deposition. In certain embodiments, the coating is plasma-enhanced chemical vapor deposition or initiated chemical vapor deposition.

As noted above, the inner surface of the container comprises a first aptamer sequence having a binding affinity for a viral vector, the sequence attached to each of at least a portion of the functional groups (i.e., attached to the fluoropolymer, as otherwise described herein). As used herein, an "aptamer sequence" comprises a nucleotide sequence that can selectively bind one or more target sites (e.g., on a viral capsid, cell surface, etc.) through non-covalent interactions (e.g., electrostatic interactions, hydrophobic interactions, shape complementation). In certain embodiments, an aptamer sequence comprises an individual oligonucleotide. In other embodiments, two or more repeats of an aptamer sequence comprise a polynucleotide.

As used herein, "viral vectors" include viruses (e.g., lentivirus, retrovirus) comprising a nucleotide sequence and capable of introducing the nucleotide sequence to a target cell. The person of ordinary skill in the art will appreciate that the surfaces of such viruses can include one or more molecules to which an aptamer sequence can bind. In certain embodiments as otherwise described herein, the first aptamer sequence has a binding affinity for the viral vector of at least 0.1 nM. For example, in certain such embodiments, the first aptamer sequence has a binding affinity for the viral vector of at least 0.25 nM, or at least 0.5 nM, 0.75 nM, or at least 1 nM, or at least 2.5 nM, or at least 5 nM, or at least 10 nM, or at least 25 nM, or at least 50 nM, or at least 75 nM, or at least 100 nM. The person of ordinary skill in the art can select a binding affinity that provides for a desirable degree of binding of a viral vector to the inner surface of the container.

In certain embodiments as otherwise described herein, the inner surface of the container further comprises a second aptamer sequence having a binding affinity for a cell receptor selected from VLA-4 and VLA-5, the sequence attached to a portion of the functional groups (i.e., attached to the fluoropolymer, as otherwise described herein). In certain embodiments as otherwise described herein, the second aptamer sequence has a binding affinity for the cell receptor of at least 0.1 nM. For example, in certain such embodiments, the first aptamer sequence has a binding affinity for the cell receptor of at least 0.25 nM, or at least 0.5 nM, 0.75 nM, or at least 1 nM, or at least 2.5 nM, or at least 5 nM, or at least 10 nM, or at least 25 nM, or at least 50 nM, or at least 75 nM, or at least 100 nM.

The person of ordinary skill in the art will appreciate that such aptamers (i.e., for both the viral vector and the target) can be prepared according to generally known procedures such as, for example, a SELEX process. The person of ordinary skill in the art can select a binding affinity that provides for a desirable degree of binding of cells of a desired type to the inner surface of the container.

By having both first aptamer sequences and second aptamer sequences bound at the inner surface of a container, a viral vector and a cell which is desired to be transduced with the viral vector can be co-located near one another, thereby simplifying the transduction As described in more detail below, the aptamers sequences can be separately bound to the surface in separate aptamer molecules, or in other embodiments can be provided together in the same aptamer molecule.

In certain embodiments as otherwise described herein, the first aptamer sequence is at least 5 basepairs in length. For example, in certain such embodiments, the first aptamer sequence is at least 10, or at least 15, or at least 20, or at least 25, or at least 30 basepairs in length. In certain embodiments as otherwise described herein, the second aptamer sequence is at least 5 basepairs in length. For example, in certain such embodiments, the second aptamer sequence at least 10, or at least 15, or at least 20, or at least 25, or at least 30 basepairs in length.

In certain embodiments as otherwise described herein, each of at least a portion of the functional groups is directly attached (i.e., through covalent bonding) to an oligonucleotide comprising the first aptamer sequence and/or the second aptamer sequence. For example, in certain such embodiments, the inner surface comprises a plurality of oligonucleotides, each comprising the first aptamer sequence and/or the second aptamer sequence, each attached to a functional group of the fluoropolymer through a covalent bond (e.g., to an amine group). In certain such embodiments, each oligonucleotide comprises the first aptamer sequence but not the second aptamer sequence, the second aptamer sequence but not the first aptamer sequence; or both the first aptamer sequence and the second aptamer sequence. For example, in certain such embodiments, the inner surface comprises a first plurality of oligonucleotides, each comprising the first aptamer sequence, each attached to a functional group of the fluoropolymer through a covalent bond (e.g., to a an amine group), and further comprises a second plurality of oligonucleotides, each comprising the second aptamer sequence, each attached to a functional group of the fluoropolymer through a covalent bond (e.g., to an amine group). When different oligonucleotides are used for the first and second aptamer sequences they can be bound to the fluoropolymer using the same chemistry or using different chemistries. In other such embodiments, the inner surface comprises a plurality of oligonucleotides, each comprising the first aptamer sequence and the second aptamer sequence, each attached to a functional group of the fluoropolymer through a covalent bond (e.g., to a an amine group).

In other embodiments, non-covalent binding can be used to attach the aptamer sequences to the inner surface of the container, for example, using non-covalent associations such as (strep)avidin/biotin.

In certain embodiments as otherwise described herein, the average concentration of oligonucleotides (e.g., comprising the first aptamer sequence and/or the second aptamer sequence) at the inner surface of the container is at least 50 oligonucleotides per square micron of surface. For example, in certain embodiments, the average concentration of oligonucleotides is at least 60, at least 70, at least 80, at least 90, at least 100, at least 250, at least 500, at least 750, or at least 1,000 oligonucleotides per square micron of inner surface of the container. The person of ordinary skill in the art will select oligonucleotide concentration(s) that provide a desired degree of viral vector and cell binding to allow for a desired degree of transduction.

In certain embodiments as otherwise described herein, each of at least a portion of the functional groups is directly attached to a polynucleotide comprising two or more repeats of the first aptamer sequence. For example, in certain such embodiments, the inner surface comprises a plurality of polynucleotides, each comprising two or more repeats of the first aptamer sequence, each attached to a functional group of the fluoropolymer through a covalent bond (e.g., to an amine group). In certain such embodiments, each polynucleotide comprises at least 10, or at least 25, or at least 50, or at least 75, or at least 100, or at least 200, or at least 300, or at least 400, or at least 500, or at least 750, or at least 1000 repeats of the first aptamer sequence.

Similarly, in certain embodiments as otherwise described herein, each of a portion of the functional groups is directly attached to a polynucleotide comprising two or more repeats of the second aptamer sequence. For example, in certain such embodiments, the inner surface comprises a first plurality of polynucleotides, each comprising two or more repeats of the first aptamer sequence, each attached to a functional group of the fluoropolymer through a covalent bond (e.g., to an amine group), and further comprises a second plurality of polynucleotides, each comprising two or more repeats of the second aptamer sequence, each attached to a functional group of the fluoropolymer through a covalent bond (e.g., to an amine group). In certain such embodiments, each polynucleotide comprises at least 10, or at least 25, or at least 50, or at least 75, or at least 100, or at least 200, or at least 300, or at least 400, or at least 500, or at least 750, or at least 1000 repeats of the first aptamer sequence or the second aptamer sequence.

Polynucleotides comprising multiple repeats of given aptamer sequences can be made via rolling circle amplification (RCA) of a template corresponding to the desired aptamer sequence, beginning from a nucleotide primer covalently attached to the fluoropolymer (e.g., through an amine group).

In certain embodiments as otherwise described herein, each of at least a portion of the functional groups is directly attached to a polynucleotide comprising at least one repeat of each of the first aptamer sequence and the second aptamer sequence. For example, in certain such embodiments, the polynucleotide is the product of rolling circle amplification (RCA) of a template corresponding to the first aptamer sequence and the second aptamer sequence in series, beginning from a nucleotide primer covalently attached to the fluoropolymer (e.g., through an amine group). In certain such embodiments, each polynucleotide comprises at least 10, or at least 25, or at least 50, or at least 75, or at least 100, or at least 200, or at least 300, or at least 400, or at least 500, or at least 750, or at least 1000 total repeats of the first aptamer sequence and the second aptamer sequence. In certain embodiments, the polynucleotide comprises an alternating series of repeats of the first aptamer sequence and the second aptamer sequence. Of course, in other embodiments, the polynucleotide comprises one or more blocks of two or more repeats of the first aptamer sequence in series, and one or more blocks of two or more repeats of the second aptamer sequence in series.

In certain such embodiments, the average concentration of polynucleotides (e.g., comprising repeats of the first aptamer sequence and/or the second aptamer sequence) comprising the inner surface of the container is at least 50 polynucleotides per square micron of surface. For example, in certain embodiments, the average concentration of polynucleotides is at least 60, at least 70, at least 80, at least 90, at least 100, at least 250, at least 500, at least 750, or at least 1,000 polynucleotides per square micron of inner surface of the container.

In certain embodiments as otherwise described herein, each of at least a portion of the functional groups is attached through a linker to at least one oligonucleotide comprising the first aptamer sequence. In certain such embodiments, the linker comprises a polypeptide or a polynucleotide. For example, in certain embodiments, the inner surface comprises a plurality of linkers (e.g., a polypeptide or a polynucleotide) attached to a functional group of the fluoropolymer through a covalent bond (e.g., to an amine group), each linker attached to at least one oligonucleotide comprising the first aptamer sequence. In certain embodiments as otherwise described herein, each of a portion of the functional groups is attached through a linker to at least one oligonucleotide comprising the second aptamer sequence. For example, in certain such embodiments, the inner surface comprises a first plurality of linkers (e.g., a polypeptide or a polynucleotide) attached to the fluoropolymer through a covalent bond (e.g., to an amine group), each linker attached to at least one oligonucleotide comprising the first aptamer sequence, and further comprises a second plurality of linkers (e.g., a polypeptide or a polynucleotide) attached to a functional group of the fluoropolymer through a covalent bond (e.g., to an amine group), each linker attached to at least one oligonucleotide comprising the second aptamer sequence. In another example, in certain such embodiments, the inner surface comprises a plurality of linkers (e.g., a polypeptide or a polynucleotide) attached to a functional group of the fluoropolymer through a covalent bond (e.g., to an amine group), each linker attached to at least one oligonucleotide comprising the first aptamer sequence and at least one oligonucleotide comprising the second aptamer sequence. Linkers can also be used with non-covalent interactions, e.g., through (strep)avidin/biotin interactions.

In certain such embodiments, at least 2 oligonucleotides (e.g., comprising the first aptamer sequence and/or the second aptamer sequence) are attached to each of at least a portion of the linkers. For example, in certain embodiments, at least 5, at least 10, at least 20, at least 30, at least 40, or at least 50 oligonucleotides are attached to each of at least a portion of the linkers.

In certain such embodiments, the average concentration of linkers (e.g., comprising the first aptamer sequence and/or the second aptamer sequence attached thereto) comprising the inner surface of the container is at least 50 linkers per square micron of surface. For example, in certain embodiments, the average concentration of linkers is at least 60, at least 70, at least 80, at least 90, at least 100, at least 250, at least 500, at least 750, or at least 1,000 linkers per square micron of inner surface of the container.

A variety of fluoropolymers can be used at the inner surface of the containers as described herein. In certain embodiments as otherwise described herein, the inner surface of the container comprises a fluoropolymer selected from polytetrafluoroethylene (PTFE), perfluoroalkoxy (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof. For example, in certain embodiments as otherwise described herein, the inner surface of the container comprises fluorinated ethylene propylene. In certain embodiments as otherwise described herein, the inner surface of the container consists essentially of the fluoropolymer (e.g., fluorinated ethylene propylene) and the functional groups and aptamer sequences attached thereto. In certain embodiments as otherwise described herein, the fluoropolymer material at the inner surface of the container has a thickness of at least 0.0003 inches, at least 0.0004 inches, at least 0.0005 inches, at least 0.0006 inches, at least 0.001 inches, or at least 0.10 inches. For example, in certain such embodiments, the material comprising the inner surface of the container has a thickness within the range of 0.0003 inches to 0.2 inches, or 0.0003 inches to 0.1 inches, or 0.0005 inches to 0.08 inches, or 0.001 inches to 0.07 inches, or 0.001 inches to 0.05 inches, or 0.001 inches to 0.03 inches, or 0.001 inches to 0.018 inches, or 0.001 inches to 0.016 inches, or 0.001 inches to 0.014 inches, or 0.001 inches to 0.012 inches.

In certain embodiments as otherwise described herein, the material making up the container wall is a multilayer material, with a layer of fluoropolymer at the inner surface thereof, and a layer of another polymeric material (fluoropolymeric or otherwise) at the outer surface thereof. In certain embodiments as otherwise described herein, the material at the outer surface of the container has a thickness of at least 0.0005 inches, or at least 0.001 inches, or at least 0.005 inches, or at least 0.0075 inches, or at least 0.01 inches, or at least 0.02 inches, or at least 0.03 inches, or at least 0.04 inches, or at least 0.05 inches, or at least 0.06 inches, or at least 0.07 inches, or at least 0.08 inches, or at least 0.09 inches, or at least 0.1 inches, or at least 0.11 inches. For example, in certain such embodiments, the material at the outer surface of the container has a thickness within the range of 0.0005 inches to 0.2 inches, or 0.005 inches to 0.18 inches, or 0.01 inches to 0.16 inches, or 0.01 inches to 0.14 inches, or 0.01 inches to 0.12 inches, or 0.06 inches to 0.13 inches, or 0.09 inches to 0.126 inches.

In certain embodiments as otherwise described herein the outer surface of the container comprises a material other than a fluoropolymer. For example, in certain such embodiments, the material at the outer surface of the container comprises a thermoplastic polymer, a thermoplastic elastomer, a silicon, a rubber, or any combination thereof. Alternatively, the outer surface of the container can, in certain embodiments as otherwise described herein, comprise a fluoropolymer such as, for example, the fluoropolymer of the inner surface, or a different fluoropolymer. In certain such embodiments, the material at the inner surface and at the outer surface (i.e., the container wall) consists essentially of the fluoropolymer (e.g., fluorinated ethylene propylene), with the functional groups and aptamer sequences attached at the inner surface.

In certain embodiments as otherwise described herein, the container further includes an aqueous medium. The aqueous medium can be, for example, a cell culture medium comprising a viral vector (e.g., as otherwise described herein) and, optionally, a target cell. As used herein, "target cells" include cells susceptible to transduction by the viral vector. In certain embodiments, the target cell comprises one or more of VLA-4 and VLA-5 surface receptors. Accordingly, in certain embodiments as otherwise described herein, the container includes a viral vector (e.g., comprising a lentivirus or a retrovirus). In certain embodiments as otherwise described herein, the container includes a target cell (e.g., comprising one or more of VLA-4 and VLA-5 surface receptors).

Advantageously, the present inventors have determined that containers described herein can facilitate co-localization of viral vectors and target cells involved in a transduction process, desirably increasing the efficiency thereof, without requiring a user to perform a manual coating process shortly before conducting the transduction. Accordingly, another aspect of the disclosure is a transduction method, comprising including a viral vector and a target cell in a container as otherwise described herein. In certain such embodiments, the container contains an aqueous media (e.g., a cell culture media). In certain such embodiments, the viral vector comprises a lentivirus or a retrovirus. In certain such embodiments, the target cell comprises one or more of VLA-4 and VLA-5 surface receptors.

In certain embodiments as otherwise described herein, the transduction method comprises including a suspension of the viral vector in a first aqueous media (e.g., a viral vector supernatant) in the container; and then incubating the container comprising the viral vector for a first period of time. The first period of time can be any length sufficient to allow association of at least a portion of the viral vector with the first aptamer sequence of the inner surface of the container. For example, in certain embodiments, the container comprising the viral vector is incubated for at least 1 hr., or at least 2 hr., or at least 3 hr., or at least 4 hr., or at least 5 hr., for example, at a temperature within the range of 32-37° C. After incubating for the first period of time, the method includes adding a target cell (e.g., as a suspension in a second aqueous medium) to the container; and then incubating the container comprising the target cell and the viral vector for a second period of time. The second period of time can be any length sufficient to allow transduction of at least a portion of the target cells. For example, in certain embodiments, the container comprising the viral vector and the target cell is incubated for at least 6 hr., or at least 12 hr., or at least 18 hr., or at least 1 day, or at least 1.5 days, or at least 2 days, or at least 2.5 days, for example, at a temperature within the range of 35-39° C. After incubating the second period of time, the method includes collecting transduced cells from the container.

In certain such embodiments, the method further includes, after incubating the container for the first period of time, removing at least a portion of the first aqueous media; then adding a wash media to the container; and then removing at least a portion of the wash media from the container (i.e., before adding the target cell to the container).

In other embodiments, the transduction method comprises including a suspension of the viral vector and the target cell in a first aqueous media (e.g., a mixture of a viral vector supernatant and target cells) to the container, and then incubating the container comprising the target cell and the viral vector for a first period of time. The first period of time can be any length sufficient to allow transduction of at least a portion of the target cells. For example, in certain embodiments, the container comprising the viral vector and the target cell is incubated for at least 6 hr., or at least 12 hr., or at least 18 hr., or at least 1 day, or at least 1.5 days, or at least 2 days, or at least 2.5 days, for example, at a temperature within the range of 35-39° C. After incubating for the first period of time, the method includes collecting transduced cells from the container.

In certain embodiments as otherwise described herein, collecting transduced cells includes removing a suspension of transduced cells from the container. In certain embodiments, collecting transduced cells comprises adding a cell dissociation medium to the container (e.g., after removing at least a portion of the transduction medium from the container), and then removing a suspension of transduced cells in the cell dissociation medium from the container. The cell dissociation can include one or more dissociation agents capable of releasing target cells from the inner surface of the container. For example, in certain such embodiments, the cell dissociation media comprises one or more of salts and chelating agents (e.g., that can disrupt binding of the second aptamer sequence to the target cell). In another example, in certain such embodiments, the cell dissociation media comprises one or more restriction enzymes (e.g., that can degrade an oligo- or polynucleotide comprising the second aptamer sequence). In another example, in certain such embodiments, the cell dissociation media comprises an oligo- or polynucleotide comprising a nucleotide sequence that is complimentary to the second aptamer sequence (e.g., that can displace a bound target cell from the second aptamer sequence).

Various aspects and embodiments of the disclosure are provided by the following enumerated listing of embodiments, which can be combined in any number and in any combination not logically or scientifically inconsistent.

Embodiment 1. A container (e.g., a bag) having an outer surface and an inner surface, the inner surface comprising
  a fluoropolymer;
  attached to the fluoropolymer, a plurality of functional groups; and
  attached to each of at least a portion of the functional groups, a first aptamer sequence having a binding affinity for a viral vector.

Embodiment 2. The container of embodiment 1, wherein the inner surface further comprises, attached to a portion of the functional groups, a second aptamer sequence having a binding affinity for a cell receptor selected from VLA-4 and VLA-5.

Embodiment 3. The container of embodiment 1 or 2, wherein each of at least a portion of the functional groups is directly attached to an oligonucleotide comprising the first aptamer sequence and/or the second aptamer sequence.

Embodiment 4. The container of embodiment 1 or 2, wherein each of at least a portion of the functional groups is directly attached to a polynucleotide comprising two or more repeats of the first aptamer sequence or the second aptamer sequence.

Embodiment 5. The container of embodiment 4, wherein the polynucleotide comprises at least one repeat of each of the first aptamer sequence and the second aptamer sequence.

Embodiment 6. The container of embodiment 4 or 5, wherein the polynucleotide comprises at least 10, at least 100, or at least 500 repeats of the first aptamer sequence or the second aptamer sequence.

Embodiment 7. The container of embodiment 1 or 2, wherein each of at least a portion of the functional groups is attached through a linker to at least one oligonucleotide comprising the first aptamer sequence and/or the second aptamer sequence.

Embodiment 8. The container of embodiment 7, wherein each of at least a portion of the functional groups is attached through a linker to at least one oligonucleotide comprising the first aptamer sequence and at least one oligonucleotide comprising the second aptamer sequence.

Embodiment 9. The container of embodiment 7 or 8, wherein at least 2, at least 5, at least 10, or at least 50 oligonucleotides are attached to each of at least a portion of the linkers.

Embodiment 10. The container of embodiment 7 or 8, wherein the linker comprises a polypeptide or a polynucleotide.

Embodiment 11. The container of any of embodiments 1-10, wherein the functional groups are the product of etching of the fluoropolymer.

Embodiment 12. The container of embodiment 11, wherein the etching is chemical etching, physical-mechanical etching, or plasma etching.

Embodiment 13. The container of any of embodiments 1-10, wherein the functional groups are the product of activation of the fluoropolymer in the presence of a reactive species.

Embodiment 14. The container of embodiment 13, wherein
  the activation is plasma activation or corona activation;
  and the reactive species comprises one or more reactive hydrocarbon vapors.

Embodiment 15. The container of embodiment 13, wherein
  the activation is plasma activation; and
  the reactive species comprises one or more polymerizable hydrocarbon vapors (e.g., selected from butylene, ethylene, and glutaraldehyde).

Embodiment 16. The container of any of embodiments 1-10, wherein the functional groups are the product of chemically treating an activated fluoropolymer.

Embodiment 17. The container of embodiment 16, wherein
  the activated fluoropolymer is the product of plasma activation or corona activation; and
  the chemical treatment is grafting polymerization, coupling, click chemistry, condensation, or addition.

Embodiment 18. The container of any of embodiments 1-10, wherein the functional groups are the product of coating an activated fluoropolymer.

Embodiment 19. The container of embodiment 18, wherein
  the activated fluoropolymer is the product of plasma activation or corona activation; and
  the coating is wet coating, powder coating, or chemical vapor deposition.

Embodiment 20. The container of any of embodiments 1-19, wherein the functional groups include one or more of carboxy groups, hydroxyl groups, aldehyde groups, carbonyl groups, amine groups, imine groups, amide groups, ester groups, anhydride groups, thiol groups, disulfides groups, phenol groups, guanidine groups, thioether groups, indole groups, imidazole groups, aminoethyl amide groups, alkyne groups, alkene groups, aziridine groups, epoxy groups, isonitrile groups, isocyanide groups, tetrazine groups, diazonium surface groups, alkyne groups, alkene groups, aziridine groups, epoxy groups, isonitrile groups, isocyanide groups, tetrazine groups, alkyl groups, aminoethyl amide groups, or ester groups.

Embodiment 21. The container of any of embodiments 1-19, wherein the functional groups include one or more of carboxy groups, hydroxyl groups, aldehyde groups, amine groups, imine groups, amide groups and ester groups.

Embodiment 22. The container of any of embodiments 1-19, wherein the functional groups include amine groups.

Embodiment 23. The container of any of embodiments 1-22, wherein the attachment of the functional group (e.g., to the oligomer, polynucleotide, or linker) is covalent.

Embodiment 24. The container of any of embodiments 1-23, wherein the fluoropolymer is polytetrafluoroethylene (PTFE), perfluoroalkoxy (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof.

Embodiment 25. The container of any of embodiments 1-23, wherein the fluoropolymer is fluorinated ethylene propylene.

Embodiment 26. The container of any of embodiments 1-25, wherein the fluoropolymer has a TOC in water of less than 0.1 mg/cm$^2$.

Embodiment 27. The container of any of embodiments 1-26, wherein the viral vector comprises a lentivirus or a retrovirus.

Embodiment 28. The container of any of embodiments 1-27, containing an aqueous media.

Embodiment 29. The container of embodiment 28, containing a viral vector (e.g., comprising a lentivirus or a retrovirus).

Embodiment 30. The container of embodiment 28 or 29, containing a target cell (e.g., comprising one or more of VLA-4 and VLA-5 surface receptors).

Embodiment 31. A transduction method, comprising including a viral vector and a target cell to the container of any of embodiments 1-29.

Embodiment 32. The transduction method of embodiment 31, wherein the viral vector comprises a lentivirus or a retrovirus.

Embodiment 33. The transduction method of embodiment 31 or 32, wherein the target cell comprises one or more VLA-4 or VLA-5 surface receptors.

Embodiment 34. The transduction method of any of embodiments 31-33, comprising
  including a suspension of the viral vector in a first aqueous medium to the container;
  incubating the container comprising the viral vector for a first period of time;
  adding a the target cell (e.g., as a suspension in a second aqueous medium) to the container;
  incubating the container comprising the target cell and the viral vector for a second period of time; and then
  collecting transduced cells from the container.

Embodiment 35. The transduction method of embodiment 34, further comprising, after incubating the container for the first period of time
  removing at least a portion of the first aqueous media; then
  adding a wash media to the container; then
  removing at least a portion of the wash media from the container; and then
  adding the target cell to the container.

Embodiment 36. The transduction method of any of embodiments 31-33, comprising
  including a suspension of the viral vector and the target cell in a first aqueous media to the container;
  incubating the container comprising the target cell and the viral vector for a first period of time; and then
  collecting transduced cells from the container.

Embodiment 37. The transduction method of any of embodiments 31-36, wherein collecting transduced cells from the container comprises
  adding a cell dissociation media to the container; and then
  removing a suspension of transduced cells from the container.

Embodiment 38. The transduction method of embodiment 37, wherein the cell dissociation media comprises one or more of salts and chelating agents.

Embodiment 39. The transduction method of embodiment 37, wherein the cell dissociation media comprises one or more restriction enzymes.

Embodiment 40. The transduction method of embodiment 37, wherein the cell dissociation media comprises an oligo- or polynucleotide comprising a nucleotide sequence that is complementary to the second aptamer sequence.

Embodiment 41. The container or method of any of embodiments 1-39, wherein the container is in the form of a bag.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Numerous references have been made to patents and printed publications throughout this specification. Each of the cited references and printed publications are individually incorporated herein by reference in their entirety.

Furthermore, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for introducing DNA to a target cell via transduction with a viral vector that is a lentivirus vector or a retrovirus vector, the method comprising
    providing a container in the form of a cell culture bag having an outer surface and an inner surface, the inner surface comprising
        a fluorinated ethylene propylene fluoropolymer;
        attached to the fluoropolymer, a plurality of functional groups;
        attached to the fluoropolymer by covalent bonding to at least a first portion of the functional groups, a first nucleotide aptamer sequence having a binding affinity for the viral vector; and
        attached to the fluoropolymer by covalent bonding to at least a second portion of the functional groups, a second nucleotide aptamer sequence having a binding affinity for a VLA-4 or VLA-5 cell receptor of the target cell; and
    incubating the viral vector and the target cell in the container, such that the viral vector is bound to the first nucleotide aptamer sequence and the target cell is bound to the second nucleotide aptamer sequence.

2. The method of claim 1, wherein the first nucleotide aptamer sequence and/or the second nucleotide aptamer sequence is provided by an oligonucleotide comprising the first nucleotide aptamer sequence and/or the second nucleotide aptamer sequence directly attached to a functional group of the surface.

3. The method of claim 1, wherein the first nucleotide aptamer sequence and/or the second nucleotide aptamer sequence is provided by a polynucleotide comprising two or more repeats of the first nucleotide aptamer sequence and/or the second nucleotide aptamer sequence directly attached to a functional group of the surface.

4. The method of claim 3, wherein the polynucleotide comprises at least one repeat of each of the first aptamer sequence and the second aptamer sequence.

5. The method of claim 3, wherein the polynucleotide comprises at least 10 repeats of the first aptamer sequence or the second aptamer sequence.

6. The method of claim 1, wherein the first nucleotide aptamer sequence and/or the second nucleotide aptamer sequence is provided by at least one oligonucleotide comprising the first nucleotide aptamer sequence and at least one oligonucleotide comprising the second nucleotide aptamer sequence, each attached to a functional group of the surface through a linker, wherein at least 10 oligonucleotides are attached to the surface.

7. The method of claim 1, wherein the functional groups are the product of etching of the fluoropolymer; the product of activation of the fluoropolymer in the presence of a reactive species; or the product of chemically treating an activated fluoropolymer.

8. The method of claim 1, wherein the functional groups include one or more of carboxy groups, hydroxyl groups, aldehyde groups, amine groups, imine groups, amide groups and ester groups.

9. The method of claim 1, wherein the functional groups include amine groups.

10. The method of claim 1, wherein the viral vector comprises a lentivirus vector.

11. The method of claim 1, comprising
including a suspension of the viral vector in a first aqueous medium to the container;
incubating the container comprising the viral vector for a first period of time;
adding the target cell to the container;
incubating the container comprising the target cell and the viral vector for a second period of time; and then
collecting transduced cells from the container.

12. The method of claim 11, further comprising, after incubating the container for the first period of time
removing at least a portion of the first aqueous media; then
adding a wash media to the container; then
removing at least a portion of the wash media from the container; and then
adding the target cell to the container.

13. The transduction method of claim 11, wherein collecting transduced cells from the container comprises
adding a cell dissociation media to the container; and then
removing a suspension of transduced cells from the container.

14. The method of claim 1, comprising
including a suspension of the viral vector and the target cell in a first aqueous media to the container;
incubating the container comprising the target cell and the viral vector for a first period of time; and then
collecting transduced cells from the container.

15. The method of claim 1, wherein the viral vector comprises a retrovirus vector.

16. The method of claim 1, wherein the functional groups are the product of activation of the fluoropolymer by plasma activation or corona activation in the presence of a reactive hydrocarbon species.

* * * * *